United States Patent
El Fray et al.

(10) Patent No.: US 9,228,043 B2
(45) Date of Patent: Jan. 5, 2016

(54) APPLICATION OF COMPOSITION CONTAINING TELECHELIC MACROMER AND PHOTOINITIATOR FOR PRODUCING IMPLANT FOR HERNIA REPAIR

(71) Applicant: ZACHODNIOPOMORSKI UNIWERSYTET TECHNOLOGICZNY W SZCZECINIE, Szczecin (PL)

(72) Inventors: Miroslawa El Fray, Dobra (PL); Jedrzej Skrobot, Ilawa (PL); Labib Zair, Gryfino (PL)

(73) Assignee: ZACHODNIOPOMORSKI UNIWERSYTET TECHNOLOGY W SZCZECINIE, Szcecin (PL)

( * ) Notice: Subject to any disclaimer, the term of this patent is extended or adjusted under 35 U.S.C. 154(b) by 49 days.

(21) Appl. No.: 13/727,876

(22) Filed: Dec. 27, 2012

(65) Prior Publication Data

US 2014/0187661 A1    Jul. 3, 2014

(51) Int. Cl.
| | | |
|---|---|---|
| C08F 222/10 | (2006.01) | |
| A61L 31/14 | (2006.01) | |
| A61L 31/04 | (2006.01) | |

(Continued)

(52) U.S. Cl.
CPC .......... *C08F 222/1006* (2013.01); *A61K 9/0024* (2013.01); *A61L 31/048* (2013.01); *A61L 31/148* (2013.01); *A61F 2/0063* (2013.01); *A61L 2400/06* (2013.01)

(58) Field of Classification Search
CPC .......... C08F 2222/1006; A61L 31/148; A61L 31/048; A61L 2400/06; A61F 2/0063; A61K 9/0024

See application file for complete search history.

(56) References Cited

U.S. PATENT DOCUMENTS

| | | | | |
|---|---|---|---|---|
| 4,490,497 A | * | 12/1984 | Evrard et al. | 523/116 |
| 4,919,151 A | | 4/1990 | Grubbs et al. | 128/898 |

(Continued)

FOREIGN PATENT DOCUMENTS

| | | | |
|---|---|---|---|
| WO | WO 99/19003 | 4/1999 | ............. A61L 25/00 |
| WO | WO 2005/055958 A2 | 6/2005 | |

OTHER PUBLICATIONS

*Syntehsis and degradation of novel photocrosslinkable aromatic copolyanhydrides*; Nagata et al.; European Polymer Journal 42; Aug. 2006; pp. 2617-2622 (www.sciencedirect.com).

(Continued)

*Primary Examiner* — Sanza McClendon
(74) *Attorney, Agent, or Firm* — Renner Kenner Greive Bobak Taylor & Weber

(57) ABSTRACT

The present invention relates to an application of a composition containing telechelic macromer and photoinitiator for producing implant for hernia repair. The macromer structure is defined by Formula 1. The macromer bears (meth)acrylic end-groups and comprises a core Y defined by Formulas 2 to 9, that is linked by urethane, ester or anhydride bonds to the (meth)acrylic groups. The iodine value of the macromer is from 5 to 75. The composition according to the present invention can be shaped at room temperature and at 37° C. and is capable of undergoing liquid-to-solid transition upon irradiation with low intensity light. Upon irradiation with light the composition gains desired physicochemical properties and turns into an elastic solid. The implant for hernia repair serves for closing the hernia opening and for enhancing mechanical strength of abdominal wall.

19 Claims, 2 Drawing Sheets

(51) Int. Cl.
*A61K 9/00* (2006.01)
*A61F 2/00* (2006.01)

(56) References Cited

U.S. PATENT DOCUMENTS

| | | | | |
|---|---|---|---|---|
| 5,290,217 | A | 3/1994 | Campos | 600/37 |
| 5,634,931 | A | 6/1997 | Kugel | 606/151 |
| 6,176,863 | B1 | 1/2001 | Kugel et al. | 606/151 |
| 6,747,088 | B1 | 6/2004 | Schwalm et al. | 524/507 |
| 2005/0202067 | A1 | 9/2005 | Lendlein et al. | 424/443 |
| 2008/0258345 | A1 | 10/2008 | Bens et al. | 264/401 |
| 2008/0318188 | A1 | 12/2008 | Stansbury et al. | 433/215 |
| 2009/0074868 | A1 | 3/2009 | Elisseeff et al. | 424/486 |
| 2009/0209717 | A1 | 8/2009 | Kelch et al. | 526/319 |
| 2009/0270999 | A1 | 10/2009 | Brown | 623/23.72 |
| 2009/0324666 | A1 | 12/2009 | Krongauz et al. | 424/409 |
| 2010/0179576 | A1 | 7/2010 | Halevy | 606/151 |
| 2011/0021695 | A1 | 1/2011 | Akiyama et al. | 524/590 |
| 2011/0184407 | A1 | 7/2011 | Craig | 606/41 |

OTHER PUBLICATIONS

*Dimethacrylate Derivatives of Dimer Acid*; Trujillo-Lemon et al; Published online in Wiley InterScience (www.interscience.wiley.com); May 2006; Journal of Polymer Science; Part A: Polymer Chemistry, vol. 44; 3921-3929

*Synthesis and characterization of telechelic macromers containing fatty acid derivatives*; El Fray et al.; Reactive & Functional Polymers 72; Jul. 31, 2012; 781-790.

Office Action mailed Apr. 6, 2015 in corresponding U.S. Appl. No. 13/727,859.

Response filed Jun. 3, 2015 in corresponding U.S. Appl. No. 13/727,859.

*Synthesis and preliminary crosslinking studies of new photocurable poly(ester-urethane)s for biomedical applications*; Skrobot et al.; Chemical Abstracts Service, Columbus, Ohio; Polish Jourlan of Applied Chemistry; vol. 53, No. 2; 2009; pp. 175-180; Database accession No. 154:268423.

*Photosensitive injectable systems for biomedical applications*; Skrobot et al.; Polimery, Instytyt Chemii Przemysowej, Warsaw, PL; vol. 55, No. 4; Jan. 2010; pp. 267-276.

*Review: Photopolymerizable and Degradable Biomaterials for Tissue Engineering Applications*; Ifkovitis et al.; Tissue Engineering; vol. 13, No. 10; Oct. 2007; pp. 2369-2385.

European Search Report mailed Jan. 12, 2015 in application No. 12186538.0.

European Search Report mailed Jun. 18, 2013 in application No. 12186536.4.

\* cited by examiner

APPLICATION OF COMPOSITION CONTAINING TELECHELIC MACROMER AND PHOTOINITIATOR FOR PRODUCING IMPLANT FOR HERNIA REPAIR

TECHNICAL FIELD

The present invention relates to the application of a composition containing telechelic macromer and photoinitiator for producing implant for hernia repair. The role of the implant is to close the hernia opening and to enhance mechanical strength of abdominal wall.

BACKGROUND ART

There are numerous patent applications and literature reports on implants for reinforcing the area of treated hernia. These implants are in the form of a patch made of fine sheet of mesh, which in most cases is made of polypropylene. After the lining of the abdominal cavity has been cut through, this polypropylene mesh is inserted into the site of hernia opening and is sutured to deep fascia of abdominal muscles.

A method of hernia treatment with the help of polypropylene mesh has been revealed in U.S. Pat. No. 5,290,217. According to this invention, the mesh is inserted into the herniated area using laparoscopic technique and is then fastened to tissues with the use of special clips. U.S. Pat. No. 5,634,931 discloses a mesh made of perlon fiber. This mesh is tightened by an elastic fiber stitched along its edges. U.S. Pat. No. 6,176,863 reports on a two-layer repair patch. The first and second layers are joined together by a seam that defines a periphery of a pouch between the layers. A resilient monofilament L-shaped spring is located within the pouch at the seam for urging the patch to conform to the generally planar configuration. Polish pending patent application P395338 reports on a composition containing telechelic macromer and photoinitiator. The present invention relates to application of this composition.

SUMMARY OF THE INVENTION

In light of the foregoing, it is a first aspect of the present invention to provide an application of composition containing telechelic macromer and photoinitiator for producing implant for hernia repair.

It is another aspect of the present invention to provide an application of composition containing telechelic macromer and photoinitiator, wherein macromer defined by Formula 1 bears (meth)acrylic end-groups and comprises core Y defined by Formulas 2 to 9 that is linked by urethane, ester or anhydride groups to the (meth)acrylic groups, and wherein the macromer has iodine value in the range of 5 to 75, for producing implant for hernia repair.

BRIEF DESCRIPTION OF THE DRAWINGS

The present invention is illustrated in the following Examples, Formulas and in the Figures.

DETAILED DESCRIPTION OF THE INVENTION

Figure 1:
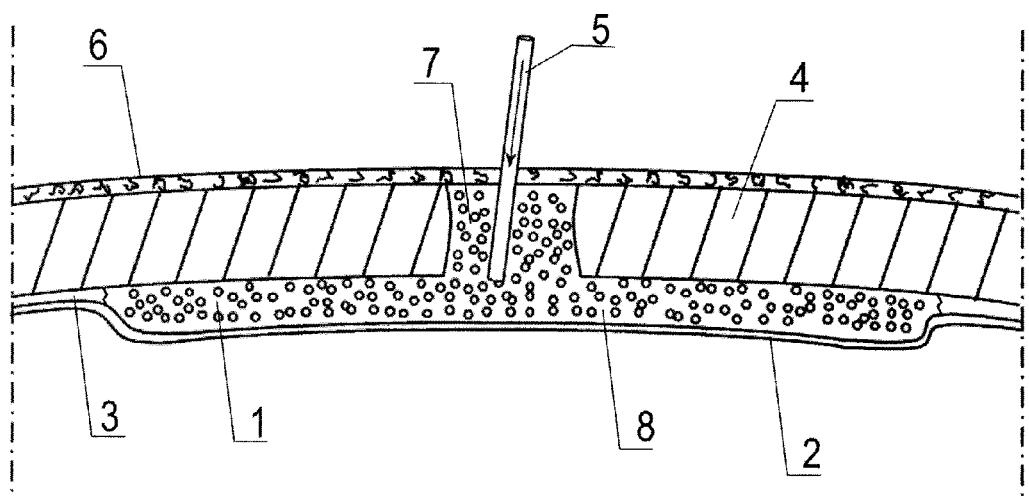
FIG. 1 represents cross-section of lining of the abdominal cavity in the hernia region at the moment of injecting the composition for producing hernia implant, in the case when the hernia opening is not closed with stitches.
Figure 2:
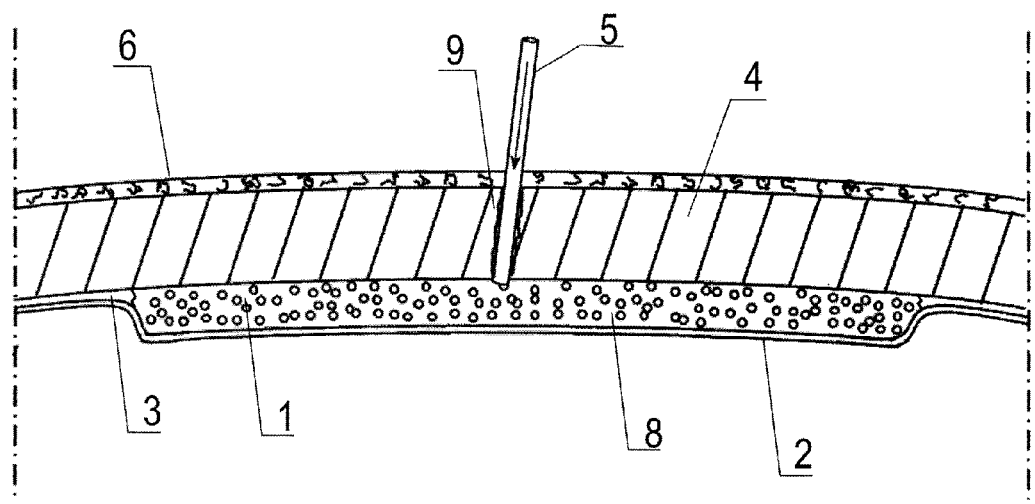
FIG. 2 represents cross-section of lining of the abdominal cavity in the hernia region at the moment of injecting the composition for producing hernia implant, in the case when the hernia opening is closed with stitches.

The present invention is illustrated in the following Examples and Formulas, wherein the Formulas are found at the end of the Detailed Description. Formula 1 shows telechelic macromer, Formula 2 shows core of macromer comprising linking ester and urethane groups, Formula 3 shows another core of macromer comprising substituents $X_1$, wherein $X_1$, $X_2$, etc can be replaced with one another to illustrate alternative sub-units of the core Y; and R, Formula 4 shows another core of macromer comprising linking ester bonds, Formula 5 shows another core of macromer comprising linking ester bonds, Formula 6 shows another core of macromer comprising linking ester bonds, Formula 7 shows another core of macromer comprising linking ester bonds, Formula 8 shows another core of macromer comprising linking ester bonds, and Formula 9 shows core of macromer comprising linking anhydride bonds.

The present invention relates to an application of a composition containing telechelic macromer and photoinitiator for producing implant for hernia repair. Said composition contains macromer defined by Formula 1, that is end-capped with (meth)acrylic groups and comprises a core Y defined by Formulas 2 to 9 and this core is linked by urethane, ester, or anhydride bonds to the (meth)acrylic groups. The iodine value of said macromer is in the range of 5 to 75. The composition is a viscous liquid or paste at room temperature and at 37° C. and is susceptible to external stimuli, such as UV/Vis light.

The precursor of the core Y defined by Formula 2 is a branched dimer fatty acid compound of 36 carbon atoms per molecule, bearing primary amine end-groups and its amine value is in the range of 200-210 mg KOH/g.

The macromer with core Y defined by Formula 2 has urethane bonds formed by a reaction of the core precursor with trimethylene carbonate or propylene carbonate and ester bonds formed by subsequent reaction with acryloyl or methacryloyl chloride.

The precursor of the core Y defined by Formula 3 comprises a branched dimer fatty acid compound of 36 carbon atoms per molecule (and then the X in Formula 3 is defined by $X_2$); or the precursor of the core Y defined by Formula 3 comprises derivatives of this dimer fatty acid which are the products of esterification of the dimer fatty acid compound with low molar mass diols of 2, 4 or 6 carbon atoms per molecule, of molar mass ranging from 540 to 2000 g/mol bearing hydroxyl end-groups and its hydroxyl value is in the range of 50-210 mg KOH/g ($X_1$); or the precursor of the core Y defined by Formula 3 comprises a linear aliphatic polyether or poly(ether-ester) of molar mass in the range of 600-2500 g/mol bearing hydroxyl end-groups ($X_4$ when it comprises a polyether and $X_3$ when it comprises a poly(ether or ester)); or the precursor of the core Y defined by Formula 3 comprises a branched polyether compound of molar mass of 1500 g/mol, bearing hydroxyl end-groups ($X_5$).

The macromer comprising core Y defined by Formula 3 has urethane bonds formed by a reaction of a precursor with 1,6-diisocyanatohexane or with 5-isocyanato-1-(isocyanatomethyl)-1,3,3-trimethylcyclohexane, or with 1,1'-methylenebis(4-isocyanatocyclohexane).

The precursor of the core Y defined by Formulas 4 or 5 is a branched dimer fatty acid compound of 36 carbon atoms per molecule, or the precursor of the core Y defined by Formulas 4 or 5 is a derivative of this dimer fatty acid which is the product of esterification of the dimer fatty acid compound with low molar mass diols of 2, 4 or 6 carbon atoms per molecule, of molar mass ranging from 540 to 2000 g/mol bearing hydroxyl end-groups and its hydroxyl value is in the range of 50-210 mg KOH/g.

The precursor of the core Y defined by Formula 6 is a linear aliphatic poly(ether-ester) of molar mass in the range of 600-2500 g/mol bearing hydroxyl end-groups.

The precursor of the core Y defined by Formula 7 is a linear aliphatic polyether of molar mass in the range of 600-2500 g/mol bearing hydroxyl end-groups.

The precursor of the core Y defined by Formula 8 is a branched polyether compound of molar mass of 1500 g/mol, bearing hydroxyl end-groups.

The telechelic macromer comprising core Y defined by Formulas 4 or 5, or 6, or 7, or 8 has linking ester bonds formed by reaction of the precursor with acryloyl or methacryloyl chloride.

The precursor of the core Y defined by Formula 9 comprises a branched dimer fatty acid compound of 36 carbon atoms per molecule, or the precursor of the core Y defined by Formula 9 comprises derivatives of this dimer fatty acid which are the products of esterification of the dimer fatty acid compound with low molar mass diols of 2, 4 or 6 carbon atoms per molecule, of molar mass ranging from 570 to 3000 g/mol bearing carboxyl end-groups and its carboxyl value is in the range of 35-210 mg KOH/g.

The telechelic macromer with core Y defined by Formula 9 comprises anhydride bonds formed by reaction of the precursor with acryloyl or methacryloyl chloride.

The photoinitiator content in said composition is in the range of 0.5-2% with respect to the total weight of the composition. Preferably, the photoinitiator is a compound having in its structure aromatic ring in position a to carbonyl group, possibly substituents at the aromatic ring or phosphine oxide group. For example, 2-hydroxy-1-[4-(2-hydroxyethoxy)phenyl]-2-methyl-1-propanone or phenylbis(2,4,6-trimethylbenzoyl)phosphine oxide, or 2,2-Dimethoxy-1,2-diphenylethan-1-one can be used.

The composition may comprise a reactive diluent, poly(ethylene glycol) diacrylate of molar mass in the range of 250-700 g/mol. The weight content of the reactive diluent in the composition varies from 1% to 99%.

The composition may comprise one or more of the three reactive diluents, trimethylolpropane triacrylate or tri(propylene glycol) diacrylate or ethoxylated trimethylolpropane triacrylate. The weight content of the reactive diluent in the composition varies from 1% to 99%. The composition comprising one or more of the three listed diluents may, additionally, comprise poly(ethylene glycol) diacrylate of molar mass in the range of 250-700 g/mol and then the weight content of said poly(ethylene glycol) diacrylate in the composition varies from 1% to 99%.

The composition may contain powder fillers such as sodium chloride, or sucrose, or a polysaccharide compound of grain size varying between 100 and 300 micrometers, wherein the filler weight content in the composition is between 30 and 80%. These fillers serve as porogens.

After the composition has been injected, it is irradiated with UV/VIS light of wavelength above 280 nm and of intensity below 50 mW/cm$^2$, which causes its cross-linking.

The composition can be injected directly as a viscous liquid or paste into the herniated area or the implant can be shaped in sterile conditions outside human body and then can be administered to the patient. In case the composition is injected into the herniated area, the viscous paste is shaped in such a manner, that its edges extend beyond the edges of the hernia opening.

An advantage of the present invention is, that the implant shape perfectly matches the shape of hernia opening and its edges extend beyond the edges of the hernia opening.

An advantage of applying said composition for producing an implant is, that the implant undergoes biodegradation in vivo. As a result of applying said composition, the time of transition from viscous liquid to hernia implant is less than 5 minutes. Another advantage of the present invention is that injecting said composition requires only slight incision of lining of the abdominal cavity, which contributes to minimizing complications after a surgery. The present invention allows for the injection and for producing implant within a short timespan, which significantly shortens the time of the surgery and the overall time of treatment.

EXAMPLES

Example I

A pasty composition containing telechelic macromer and photoinitiator is injected into the gap 1 between peritoneum 2 and deep fascia 3 of abdominal muscles 4. The composition is injected into gap 1 through small opening in skin 6, thus filling the gap 1 and the inside of hernia opening 7, thus forming patch 8 of 1-3 mm in thickness. The size of the patch, which implies the amount of injected composition, is larger than the hernia opening. The strip between the edge of implant and the edge of hernia opening is 5 to 15 mm wide.

After the patch has been formed, the composition is irradiated with UV/Vis light of wavelength above 280 nm and total intensity of 20 mW/cm$^2$, during 100 seconds. The composition is cross-linked and an elastic solid patch obtained.

Example II

The procedure is performed in a way analogous to Example I, with the difference that the hernia opening is closed with stitches 9.

Example III

A patch is formed on a Petri dish in sterile conditions outside human body from a composition containing telechelic macromer and photoinitiator. The patch has a round or elliptical shape, thickness of 1 to 3 mm and a diameter of 1 to 7 cm. The composition is irradiated with UV/Vis light of wavelength above 280 nm and total intensity of 10 mW/cm$^2$, during 200 seconds. The composition is cross-linked and an elastic solid patch is obtained. The obtained patch is rolled up to form a roll of appropriate diameter, allowing for delivering it with an applicator. The patch is delivered to the area of hernia opening which is closed with stitches 9. Then the patch is unrolled on the face of closed hernia opening and is fastened by absorbable sutures.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of the true scope and breadth of the invention, reference should be made to the following claims.

Formulas

Formula 1

$$Z\underset{C}{\overset{\parallel}{\underset{|}{C}}}-\overset{O}{\overset{\parallel}{C}}-Y-\overset{O}{\overset{\parallel}{C}}-\underset{\underset{|}{C}}{\overset{Z}{\underset{|}{C}}}$$

$Z = H, CH_3$

Formula 2

$Y = *-O-C_3H_6-O-\overset{O}{\overset{\parallel}{C}}-\underset{H}{N}-(CH_2)_{36}-\underset{H}{N}-\overset{O}{\overset{\parallel}{C}}-O-C_3H_6-O-*$ Formula 3

$Y = *-O-\begin{bmatrix}C_2H_4\\C_3H_6\end{bmatrix}-O-\overset{O}{\overset{\parallel}{C}}-\underset{H}{N}-R-\underset{H}{N}-\overset{O}{\overset{\parallel}{C}}-X-\overset{O}{\overset{\parallel}{C}}-\underset{H}{N}-R-\underset{H}{N}-\overset{O}{\overset{\parallel}{C}}-O-\begin{bmatrix}C_2H_4\\C_3H_6\end{bmatrix}-O-*$, where $X_1 = *\left[O-(CH_2)_x-O-\overset{O}{\overset{\parallel}{C}}-(CH_2)_{34}-\overset{O}{\overset{\parallel}{C}}\right]_p O-(CH_2)_x-O-*$ $x = 2, 4, 6 \quad 2 < p < 6$ $X_2 = *-O-(CH_2)_{36}-O-*$ $X_3 = *\left[O\frown O\frown O-\overset{O}{\overset{\parallel}{C}}\frown\overset{O}{\overset{\parallel}{C}}\right]_p O\frown O\frown O^*$ $3 < p < 11$ $X_4 = *\left[O\frown O\right]_n *$ $12 < n < 32$ $X_5 = H\left[O\frown\right]_y O-\underset{H_2C-O\left[\frown O\right]_z *}{\overset{H_2C-O\left[\frown O\right]_x *}{CH}}$, and $(x+y+z) \cong 24$ $R = $ (trimethylcyclohexyl group)  or  $R = *\frown\frown\frown*$  or $R = *$—(dicyclohexylmethylene)—$*$ Formula 4

$Y = *\left[O-(CH_2)_x-O-\overset{O}{\overset{\parallel}{C}}-(CH_2)_{34}-\overset{O}{\overset{\parallel}{C}}\right]_p O-(CH_2)_x-O-*$ $x = 2, 4, 6 \quad 2 < p < 6$ Formula 5

$Y = *-O-(CH_2)_{36}-O-*$

Formula 6

$Y = *\left[O\frown O\frown O-\overset{O}{\overset{\parallel}{C}}\frown\overset{O}{\overset{\parallel}{C}}\right]_p O\frown O\frown O^*$ $3 < p < 11$ Formula 7

$Y = *\frown O\left[\frown O\right]_n *$ $12 < n < 32$

-continued

Formula 8

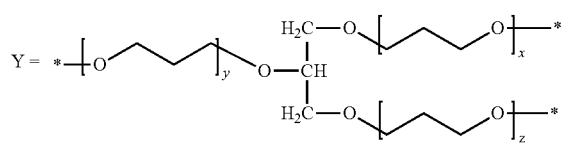

(x + y + z) ≅ 24

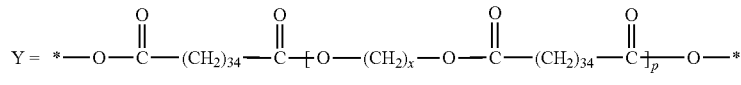

x = 2, 4, 6  2 < p < 6 or p = 0

Formula 9

What is claimed is:

1. A composition for producing an implant for hernia repair, comprising
   (A) a telechelic macromer, and
   (B) a photoinitiator,
   wherein the telechelic macromer includes a core Y linked by at least two moieties selected from the group consisting of urethane, ester, and anhydride groups,
   wherein each moiety is terminated with a (meth)acrylic end group, and
   wherein the telechelic macromer has an iodine value in the range of 5 to 75,
   wherein the core Y is selected from any of formulas (2) to (9):

(2)

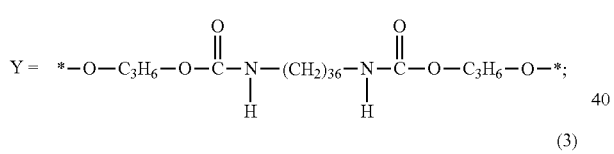

(3)

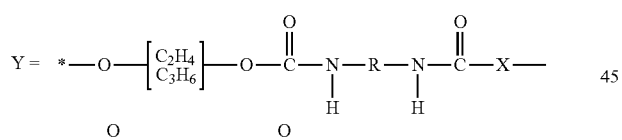

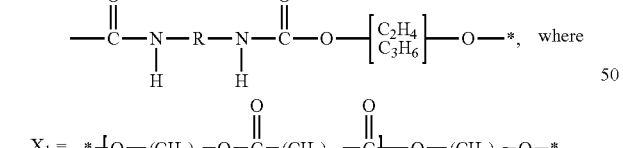

$X_1 =$ 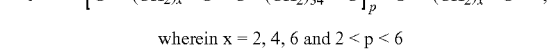, wherein x = 2, 4, 6 and 2 < p < 6

$X_2 =$ 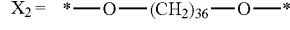

$X_3 =$ 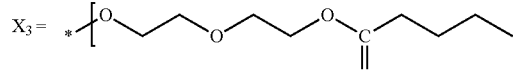 wherein 3 < p < 11

$X_4 =$ 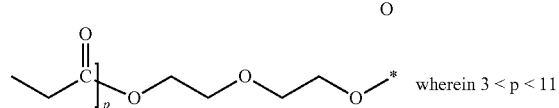 wherein 12 < n < 32

-continued $X_5 =$ 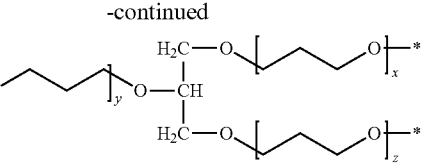

wherein (x + y + z) ≅ 24, and wherein X in the core Y is selected from the group consisting of $X_1$, $X_2$, $X_3$, $X_4$, and $X_5$, wherein R is selected from formula (I) to (III)

(I)

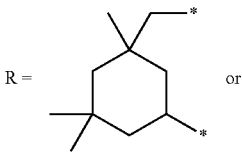 or (II)

R = 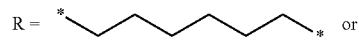 or (III)

R = 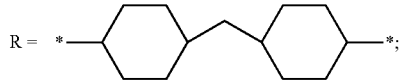;

(4)

Y = 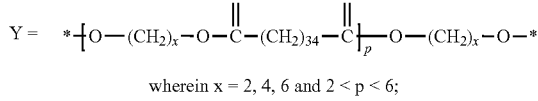

wherein x = 2, 4, 6 and 2 < p < 6;

(5)

Y = 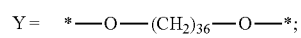;

(6)

Y = 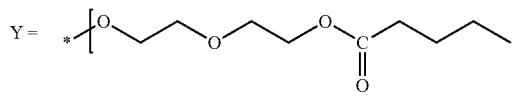 wherein 3 < p < 11;

(7)

Y = 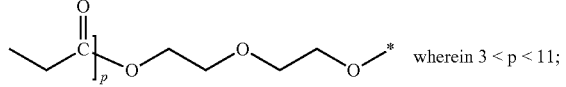 wherein 12 < n < 32;

-continued (8)
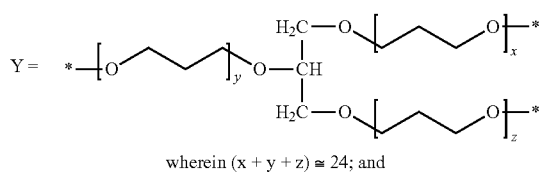

wherein (x + y + z) ≅ 24; and (9)
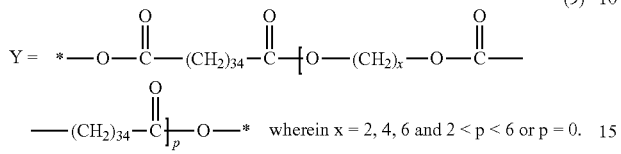

wherein x = 2, 4, 6 and 2 < p < 6 or p = 0.

2. The composition of claim 1, wherein the telechelic macromer is defined by the formula

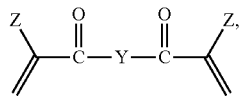

wherein each Z is selected from the group consisting of hydrogen and a methyl group, and
wherein core Y is defined by a formula (2) to (9).

3. The composition of claim 1, wherein the photoinitiator compound comprises an aromatic ring in position a to a carbonyl group, and optionally substituents at the aromatic ring and optionally a phosphine oxide group, and wherein the amount of the photoinitiator is in the range of 0.5-2 weight %.

4. The composition of claim 1, wherein the composition comprises a reactive diluent which is poly(ethylene glycol) diacrylate of molar mass in the range of 250 to 700 g/mol, and wherein the weight content of the reactive diluent in the composition varies from 1% to 99%.

5. The composition of claim 1, wherein the composition comprises a reactive diluent which is selected from one or more of the following: trimethylolpropane triacrylate, tri(propylene glycol) diacrylate, and ethoxylated trimethylolpropane triacrylate; and wherein the weight content of the reactive diluent in the composition is in the range of from 1% to 99%.

6. The composition of claim 1 or claim 4, wherein the composition comprises a powder filler selected from the group consisting of sodium chloride, sucrose, polysaccharide compound, and mixtures thereof, with a grain size in the range of from 100 to 300 micrometers, and wherein the filler weight content in the composition is in the range of from 30 to 80%.

7. The composition of claim 4, wherein the composition further comprises at least another reactive diluent which is selected from one or more of the following:
trimethylolpropane triacrylate, tri(propylene glycol) diacrylate, and ethoxylated trimethylolpropane triacrylate; and wherein the weight content of all reactive diluents in the composition is in the range of from 1% to 99%.

8. A method of preparing the composition of claim 1, comprising the step of forming the core Y using a precursor of a branched dimer fatty acid compound of 36 carbon atoms per molecule, bearing primary amine end-groups and its amine value being in the range of 200-210 mg KOH/g, the core Y thereby being defined by the formula

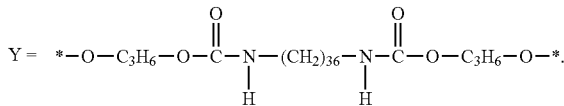

9. The method of claim 8, wherein the telechelic macromer comprises urethane bonds formed by reaction of the core precursor with trimethylene carbonate or propylene carbonate and the linking ester bonds are formed by subsequent reaction with acryloyl or methacryloyl chloride.

10. A method of preparing the composition of claim 1, comprising the step of forming the core Y using a precursor of
a branched dimer fatty acid compound of 36 carbon atoms per molecule, or
derivatives of the above dimer fatty acid, which are the products of esterification of the dimer fatty acid compound with low molar mass diols of 2, 4 or 6 carbon atoms per molecule, of molar mass ranging from 540 to 2000 g/mol bearing hydroxyl end-groups and its hydroxyl value is in the range of 50-210 mg KOH/g, or
a linear aliphatic polyether or poly(ether-ester) of molar mass in the range of 600-2500 g/mol bearing hydroxyl end-groups, or
a branched polyether compound of molar mass of 1500 g/mol, bearing hydroxyl end-groups,
the core Y thereby being defined by the formula

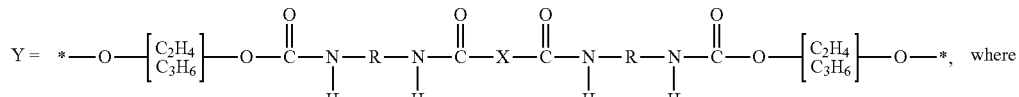, where

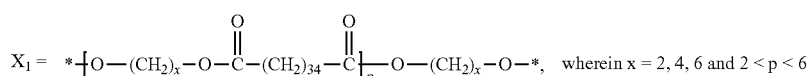, wherein x = 2, 4, 6 and 2 < p < 6

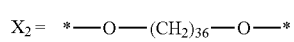

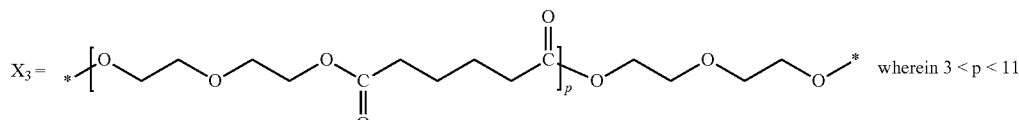 wherein 3 < p < 11

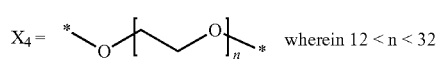 wherein 12 < n < 32

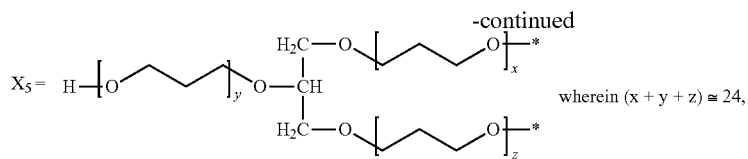

wherein (x + y + z) ≅ 24, and wherein X in the core Y is selected from the group consisting of $X_1$, $X_2$, $X_3$, $X_4$, and $X_5$, wherein R is selected from formula (I) to (III)

(I)

(II)

R = *~~~~~~* or (III)

R = *—⌬—⌬—*.

11. The method of claim 10, wherein the linking urethane bonds of the macromer are formed by reaction of the core precursor with 1,6-diisocyanatohexane, 5-isocyanato-1-(isocyanatomethyl)-1,3,3-trimethylcyclohexane, or 1,1'-methylenebis(4-isocyanatocyclohexane).

12. A method of preparing the composition of claim 1, comprising either (1) the step of forming the core Y using a precursor of a branched dimer fatty acid compound of 36 carbon atoms per molecule, the core Y thereby being defined by the formula Y = *—O—(CH$_2$)$_{36}$—O—*; or     (2)

the step of forming the core Y using a precursor of derivatives of this dimer fatty acid, which are the products of esterification of the dimer fatty acid compound with low molar mass diols of 2, 4 or 6 carbon atoms per molecule, of molar mass ranging from 540 to 2000 g/mol bearing hydroxyl end-groups and its hydroxyl value is in the range of 50-210 mg KOH/g, the core Y thereby being defined by the formula $$Y = *\!-\!\!\left[O\!-\!(CH_2)_x\!-\!O\!-\!\overset{O}{\underset{\|}{C}}\!-\!(CH_2)_{34}\!-\!\overset{O}{\underset{\|}{C}}\right]_p\!\!-\!O\!-\!(CH_2)_x\!-\!O\!-\!*$$

wherein x = 2, 4, 6 and 2 < p < 6.

13. A method of preparing the composition of claim 1, comprising the step of forming the core Y using a precursor of a linear aliphatic poly(ether-ester) of molar mass in the range of 600-2500 g/mol bearing hydroxyl end-groups, the core Y thereby being defined by the formula

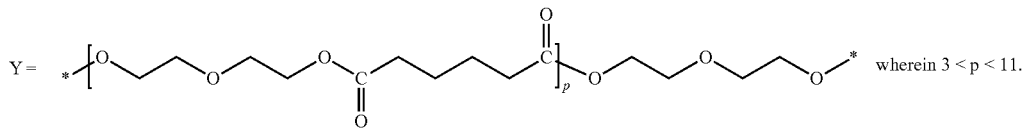

wherein 3 < p < 11.

14. A method of preparing the composition of claim 1, comprising the step of forming the core Y using a precursor of a linear polyether of molar mass in the range of 600-2500 g/mol bearing hydroxyl end-groups, the core Y thereby being defined by the formula $$Y = *\!\diagdown\!\!O\!\!\left[\diagup\!\!\diagdown\!\!O\right]_n\!\!\diagup\!*$$

wherein 12 < n < 32.

15. A method of preparing the composition of claim 1, comprising the step of forming the core Y using a precursor of a branched polyether of molar mass of 1500 g/mol bearing hydroxyl end-groups, the core Y thereby being defined by the formula

wherein (x + y + z) ≅ 24.

16. The method of claims 12-15, wherein the telechelic macromer comprises linking ester bonds that are formed by a reaction of the core precursor with (meth)acryloyl chloride.

17. A method of preparing the composition of claim 1, comprising the step of forming the core Y using a precursor of a branched dimer fatty acid compound of 36 carbon atoms per molecule, or a precursor of derivatives of this dimer fatty acid, which are the products of esterification of the dimer fatty acid compound with low molar mass diols of 2, 4 or 6 carbon atoms per molecule, of molar mass ranging from 570 to 3000 g/mol bearing carboxyl end-groups and its carboxyl value is in the range of 35-210 mg KOH/g, the core Y thereby being defined by the formula

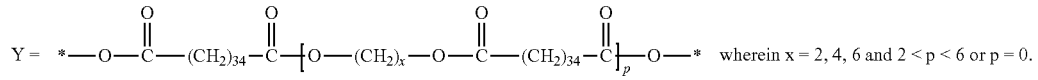

wherein $x = 2, 4, 6$ and $2 < p < 6$ or $p = 0$.

18. The method of claim 17, wherein linking anhydride bonds are formed by a reaction of the core precursor with (meth)acryloyl chloride.

19. The composition of claim 5 or claim 7, wherein the composition comprises a powder filler selected from the group consisting of sodium chloride, sucrose, polysaccharide compound, and mixtures thereof, with a grain size in the range of from 100 to 300 micrometers, and wherein the filler weight content in the composition is in the range of from 30 to 80%.

* * * * *